(12) United States Patent
Liao

(10) Patent No.: US 6,696,025 B2
(45) Date of Patent: Feb. 24, 2004

(54) MULTI-FUNCTIONAL ASSEMBLIES FOR TOILET PRODUCTS

(76) Inventor: Wayne Liao, 9Fl., No. 309, Sec. 4, Chengde Rd., Shrlin Chiu, Taipei City (TW)

(*) Notice: Subject to any disclaimer, the term of this patent is extended or adjusted under 35 U.S.C. 154(b) by 296 days.

(21) Appl. No.: 09/842,850

(22) Filed: Apr. 27, 2001

(65) Prior Publication Data

US 2002/0182120 A1 Dec. 5, 2002

(51) Int. Cl.[7] ................................................. A61L 9/00
(52) U.S. Cl. ........................... 422/123; 422/5; 222/105; 222/180; 222/192; 222/202
(58) Field of Search ..................... 422/123, 5; 222/105, 222/180, 181.3, 192, 202

(56) References Cited

U.S. PATENT DOCUMENTS

| | | | | |
|---|---|---|---|---|
| 3,865,271 A | * | 2/1975 | Gold | 221/96 |
| 4,964,543 A | * | 10/1990 | Scheiber | 222/180 |
| 5,887,759 A | * | 3/1999 | Ayigbe | 222/192 |
| 6,497,345 B1 | * | 12/2002 | Wilker et al. | 222/192 |

FOREIGN PATENT DOCUMENTS

WO    WO 93/04622    * 3/1993

* cited by examiner

Primary Examiner—Robert J. Warden, Sr.
Assistant Examiner—Sean E. Conley
(74) Attorney, Agent, or Firm—Rosenberg, Klein & Lee

(57) ABSTRACT

The invention provides a multi-functional assembly for toilet products useful in the toilet space by designing an air freshener that has functions of deodorizing and aromatizing air into an hanging assembly that can joint with other toilet products such as the toilet-paper roll, the tooth mug, the tooth brush and the like. The assembly of the invention comprises an air freshener vessel that can be fixed on the wall by a suitable manner, and is consisted of a upper part and a lower part, wherein on the lower edge of said upper part, there is disposed a protruding shaft to which, an arc pressing plate is jointed by means of a pivotally engaging hole; between said pressing plate and said air freshener vessel, it is divided into several compartments, wherein one of them is a push-type air freshener for usual use, while other compartments store the spare air freshener; the lower part of the air freshener vessel can be engaged with said upper part or can be formed together with said upper part integrally; by virtue of combining other toilet tools such as toilet paper roll holder, tooth mug holder, tooth brush holder and the like into an integral assembly having multiple functions such that not only increases the added value of the products, but also make the wall of the toilet compact and good looking.

3 Claims, 8 Drawing Sheets

PRIOR

MULTI-FUNCTIONAL ASSEMBLIES FOR TOILET PRODUCTS

BACKGROUND OF THE INVENTION

1. Field of the Invention

The invention relates to multi-functional assemblies for toilet products, and in particular, to assemblies primarily useful in the toilet space by designing an air freshener that has functions for deodorizing and aromatizing air into an hanging assembly that can joint with other toilet products such as the toilet-paper roll, the tooth mug, the tooth brush and the like.

2. Description of the Prior Art

Since an advanced and hygiene life not only must emphasize on a clean and sanitary environmental, but also should comprise organoleptic comfortableness on, for example, smelling, visual and the like, which includes a fresh and even aromatic air, an orderly spacious arrangement, and the like.

For a modern life in living house or at working place, a toilet space is undoubtedly a special, important and essential space. The particularity of a toilet space resides on its privacy where people see each other nakedly. Therefore, whether the unpleasantness on smelling or random visual scenery, will yield an immediate and direct influence on the emotion, which in turn, may affect the efficiency for dealing with people or task. Nevertheless, a toilet space is a space where it provides a variety of functions such as, for example, excretion, washing, showering, bathing, laundry and the like. For these, it inner surface of walls is often highly utilized, such as, mirror, soap dish holder, toothbrush holder, toilet-paper holder and the like. These diverse apparatuses, however, make the toilet space disorder scenery.

Product useful for providing the toilet space a fresh air, fragrance, and deodorizing is now popular and is commercially available. Among them, the most typical one was described in ROP No. 88203043, titled "An Improved Structure of Hand Pressing Air Freshener Box", as shown in FIG. 8. It is consisted essentially of a hang seat 1, a cover body 2 and a atomizer 3, and is characterized in that the base of said cover body 2 is connected pivotally with said hang seat 1, and two holding plates 22 are provided inwardly and inclined downwardly on both sides of the slot 21; and wherein said atomizer 3 is fixed inside said hang seat 2, while a cap 31 is provided about its nozzle in a manner that a shoulder 32 around said cap 31 can be held correspondingly against said holding plates on said cover body 2. Air freshener box with the above-described structure is highly popular on the market. Though, as described above, it is important to providing fresh air, fragrance and deodorizing in the toilet space, this would, additionally, put another burden on the previously highly utilized wall of the toilet space. Further, in case of improperly arrangement, unharmonious visual scenery of the toilet space would be resulted. Therefore, the problem underlying the invention is to integrate efficiently this increasingly popular commercial product with other essential tools in the toilet space into a single assembly in order to simplify and beautify the toilet space.

Further, although it might be the responsibility of a designer to provide a compact, elegant and good-looking living space, it is on the side of the general commodity designer to innovate multi-functional, space-saving 10 and efficient commodities. Accordingly, the inventor has studied extensively to integrate hanging parts used in the toilet space and as the result, accomplished finally the inventive multi-functional assembly for toilet products.

SUMMARY OF THE INVENTION

As described above, the purpose of the invention comprises at first of providing an fresh, aromatic and deodorized toilet space and further integrating essential toilet products into a single assembly, and thus provides a multi-functional, space-saving and efficient toilet assembly.

The multi-functional assembly of toilet products according to the invention comprises:

a main vessel body, consisting of a upper part and a lower part, wherein said upper part is provided with several compartments, and said lower part is extended from said upper part or is engaged with said upper part, and wherein, along the perpendicular direction on each of both lateral side of said lower part, a side plate is provided, respectively; and arc guiding slots are provided at suitable places along the inner edge of each of said two side plates;

a supporting shaft, having both ends thereof being disposed in said arc guiding slots;

a pressing plate, provided with a slot on top end thereof; and a pressing block, provided at a suitable site on its top end with a nozzle corresponding with said slot.

As described above, according to the multi-functional assembly of the invention, as the pressing plate is pushed down by a manual force, said pressing block can be pushed at the same time and it can in turn push the content such as a perfume, in the compartment to atomize said air freshener solution in said compartment out of said nozzle provided on said pressing block and release via said slot in said pressing plate, while said support shaft in said lower part can have toilet-paper roll disposed therein.

Further, in order to keep the toilet paper roll clean and not polluted by dust, a turn over cover on said lower part.

In the multi-functional assembly of toilet products according to the invention, said lower part, which can be integrally formed with said upper part or that can be joint separately with said upper part, can be varied in design depending on its end use, for example, by changing the above-described lower part holding a toilet paper roll into an assembly of soap dish holder, toothbrush holder, tooth mug holder or other related toilet products.

BRIEF DESCRIPTION OF THE DRAWINGS

The drawings disclose an illustrative embodiment of the present invention which serves to exemplify the various advantage and objects hereof, and are as follows.

Symbols representation:

| | |
|---|---|
| 10 | Air freshener vessel |
| 11 | Upper part |
| 12 | Lower part |
| 13 | Air freshener vessel compartments |
| 14 | Protruding shaft |
| 20 | Pressing plate |
| 21 | Slot |
| 22 | Pivotally engaging hole |
| 30 | Air freshener |
| 31 | Pressing block |
| 32 | Nozzle |
| 50 | Toilet paper roll holder |
| 51 | Lateral plate |
| 52 | Toilet paper roll holding shaft |
| 53 | Through hole |
| 54 | Turn over cover |
| 55 | Arc guiding slot |
| 56 | Pivotally engaging hole |
| 57 | Toilet paper roll |
| 58 | Button |
| 60 | Tooth mug holder |
| 61 | Tool holding port |
| 62 | Tooth mug |
| 70 | Tooth brush holder |
| 71 | Tool holding port |
| 72 | Tooth brush |
| 80 | Soap dish holder |
| 81 | Soap |

DETAILED DESCRIPTION OF THE PREFERRED EMBODIMENT

Various features, effects, objects and the like of the invention will be more clearly understood from the following description of preferred embodiment in conjunction with reference to the appended drawings.

As mentioned above, the invention is directed to multi-functional assemblies for toilet products primarily useful in the toilet space by designing an push-type air freshener that has functions of deodorizing and aromatizing air in the toilet space into an hanging assembly that can joint with other functional toilet products such as the toilet-paper roll, the tooth mug, the tooth brush and the like.

Figure 1:
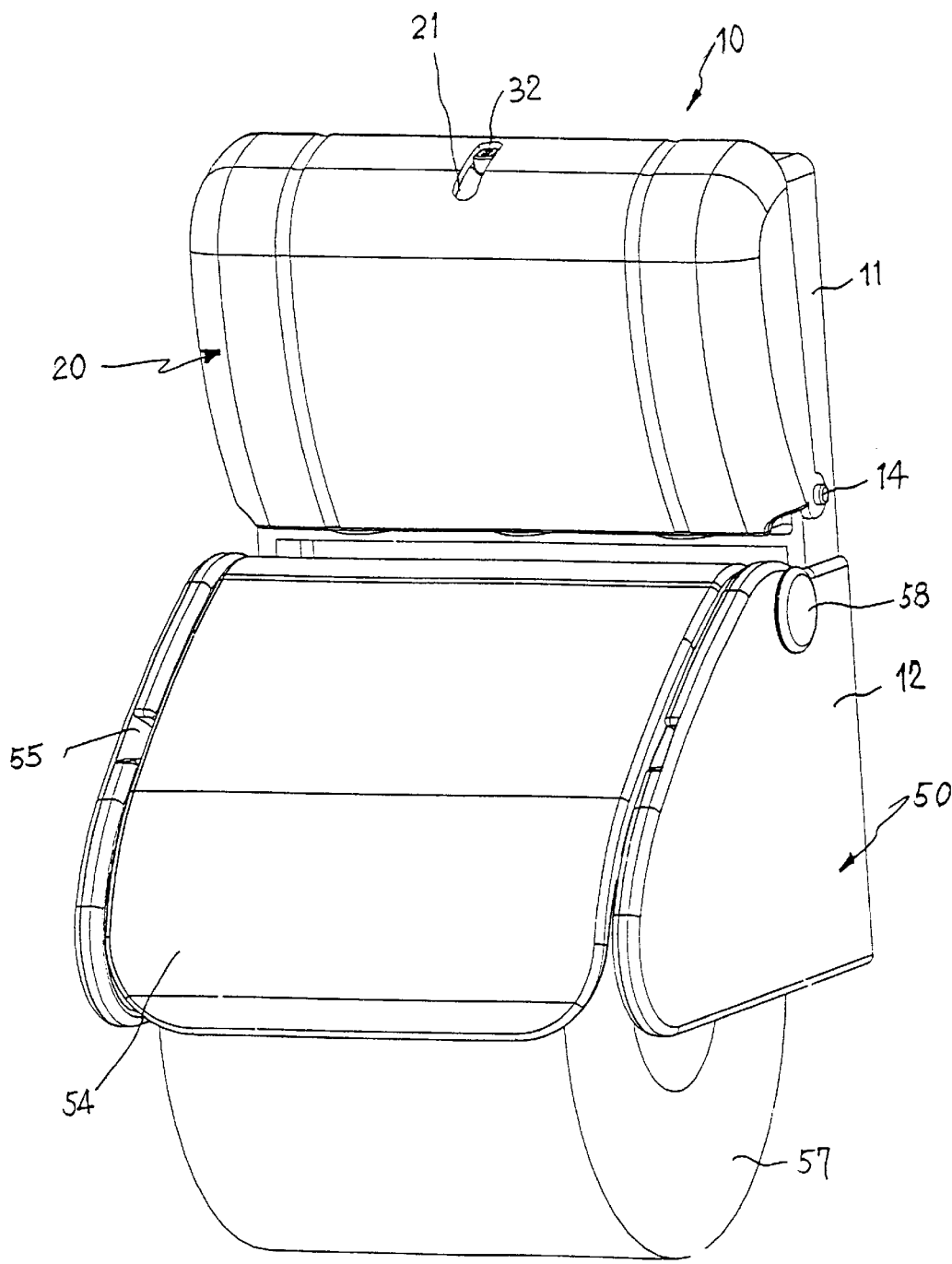
FIG. 1 is a three-dimensional view of the first embodiments according to the invention.
Figure 2:
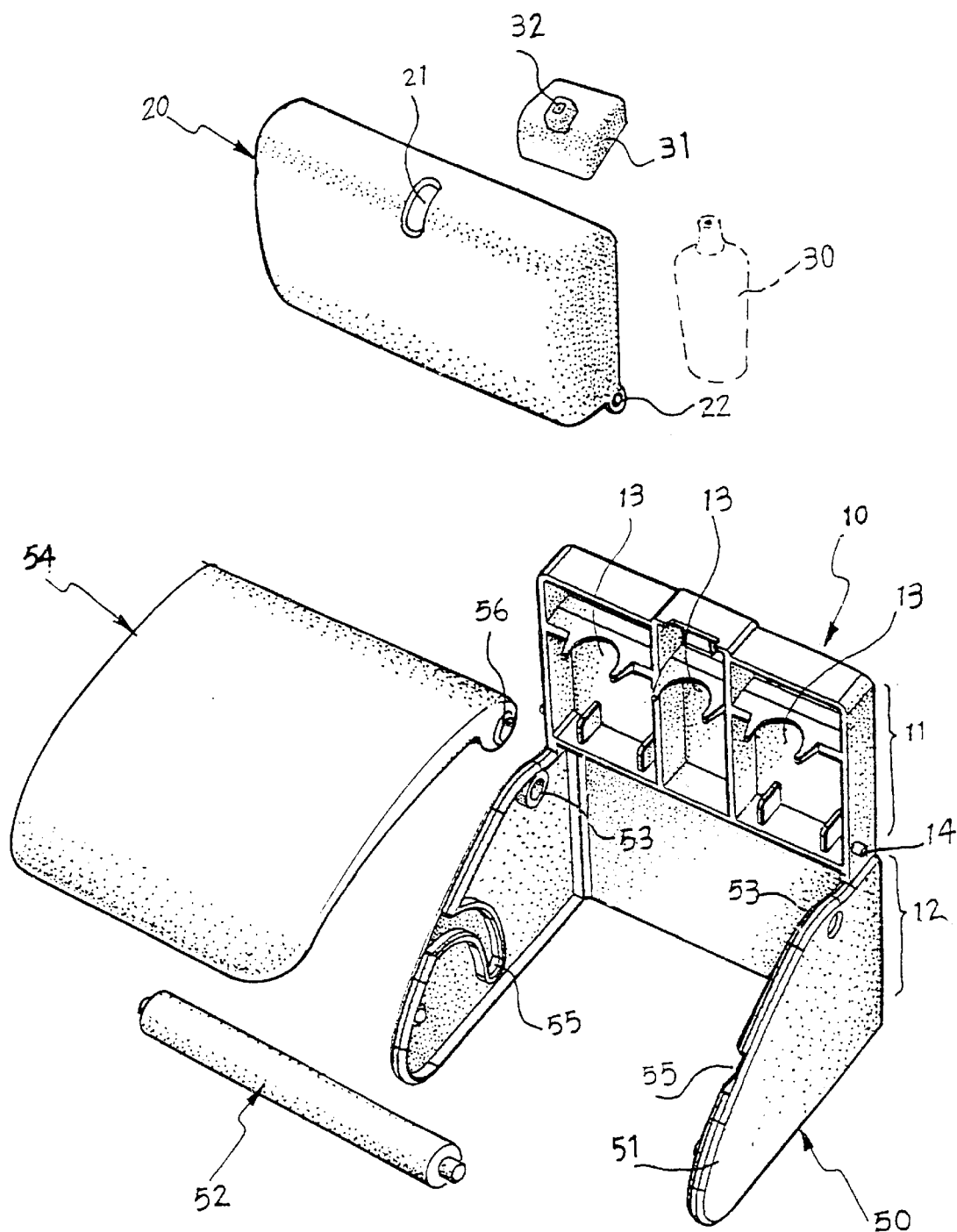
FIG. 2 is a three-dimensional exploded view of the first embodiments according to the invention.

Referring to FIGS. 1 and 2, the subject of the invention comprises a flat plate-shaped air freshener vessel 10 that can be bound with the wall and is consisted of an upper part 11 and a lower part 12. At the lower edge of aid upper part 11, a protruding shaft 14 is provided and is engaged with an arc pressing plate 20 through a pivotally engaging hole 22. Between said pressing plate 20 and said air freshener vessel 10, there are divided three air freshener vessel compartments 13. As shown in FIG. 2, the middle compartment 13 holds a push-type air freshener 30 for usual use, other two compartments 13 on both sides hold spare air fresher 30 for exchange. On the outlet of the air freshener 30, there is provided a pressing block 31 that has a protruding nozzle 32 on its top end. A slot 21 is provided above the pressing plate 20 in a manner that, after pressing said pressing plate 20, the slope at the bottom of said slot 21 can press the pressing block 31 such that the air freshener 30 will be pushed and atomized through the nozzle 32 into the air. Since the mechanism of pressing and atomizing is well known in the art, it will not further described herein.

From the toilet paper roll holder 50 combined with the lower part 12 of the air freshener vessel 10, as shown in FIGS. 1 and 2, it is apparent that the invention integrates the most important toilet paper with the air freshener. Along the inner edge of two lateral plates 51 of said toilet paper roll holder 50, there are provided arc-guiding slots 55 for supporting a toilet paper roll-supporting shaft 52 in order to hang a roll-type toilet paper 57. A turn over cover 54 is provided above these two lateral plates 51. Two pivotally engaging holes 56 at both sides of the upper edge of the turn over cover 54 is integrated with through holes 53 on the corresponding positions of the lateral plates 51 through a push button 58 in a manner that the turn over cover 54 can be turn over pivotally on the lateral plates 51 by using the push button 58 as the axis.

Figure 3:
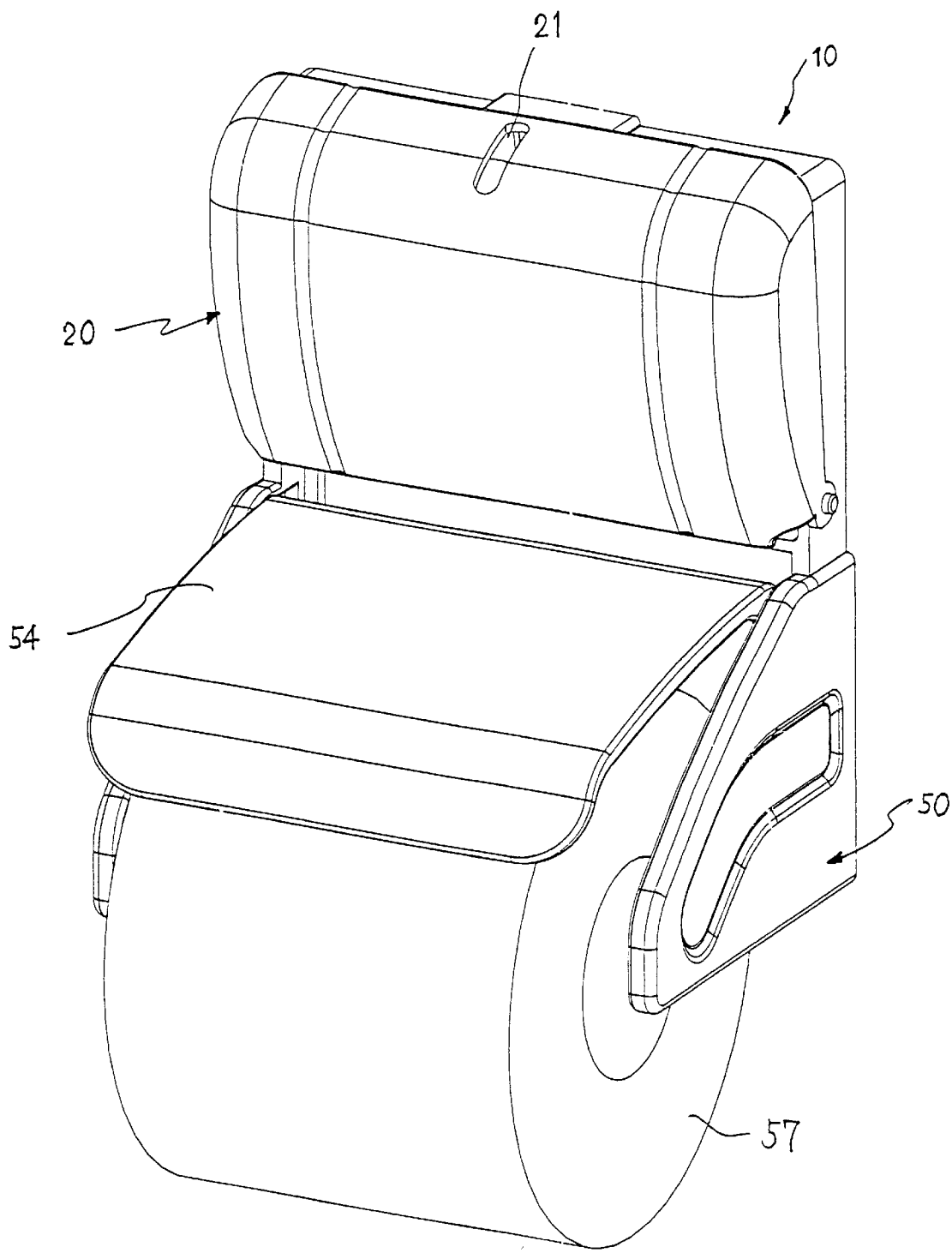
FIG. 3 is a schematic view of the second embodiments according to the invention.

Based on the concept described above, FIG. 3 shows an alternative assembly according to the invention that integrates the toilet paper roll holder 50 with an air freshener 30.

Figure 4:
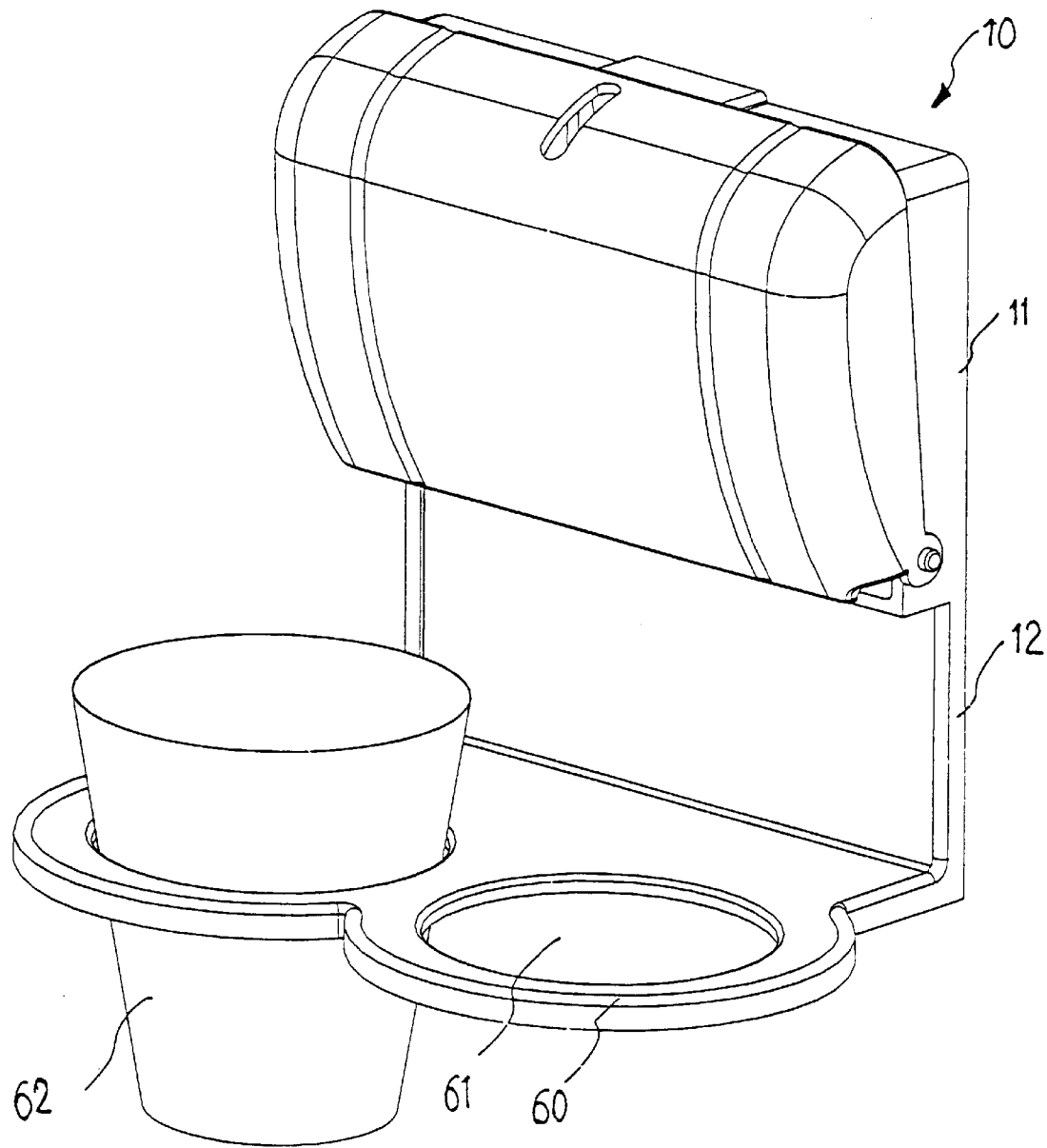
FIG. 4 is a schematic view of the third embodiments according to the invention.

In another embodiment shown in FIG. 4, the lower part 12 of the air freshener vessel 10 comprises a tooth mug holder 60 that has a holding hole 61 for holding tools such as tooth mug 62.

Figure 5:
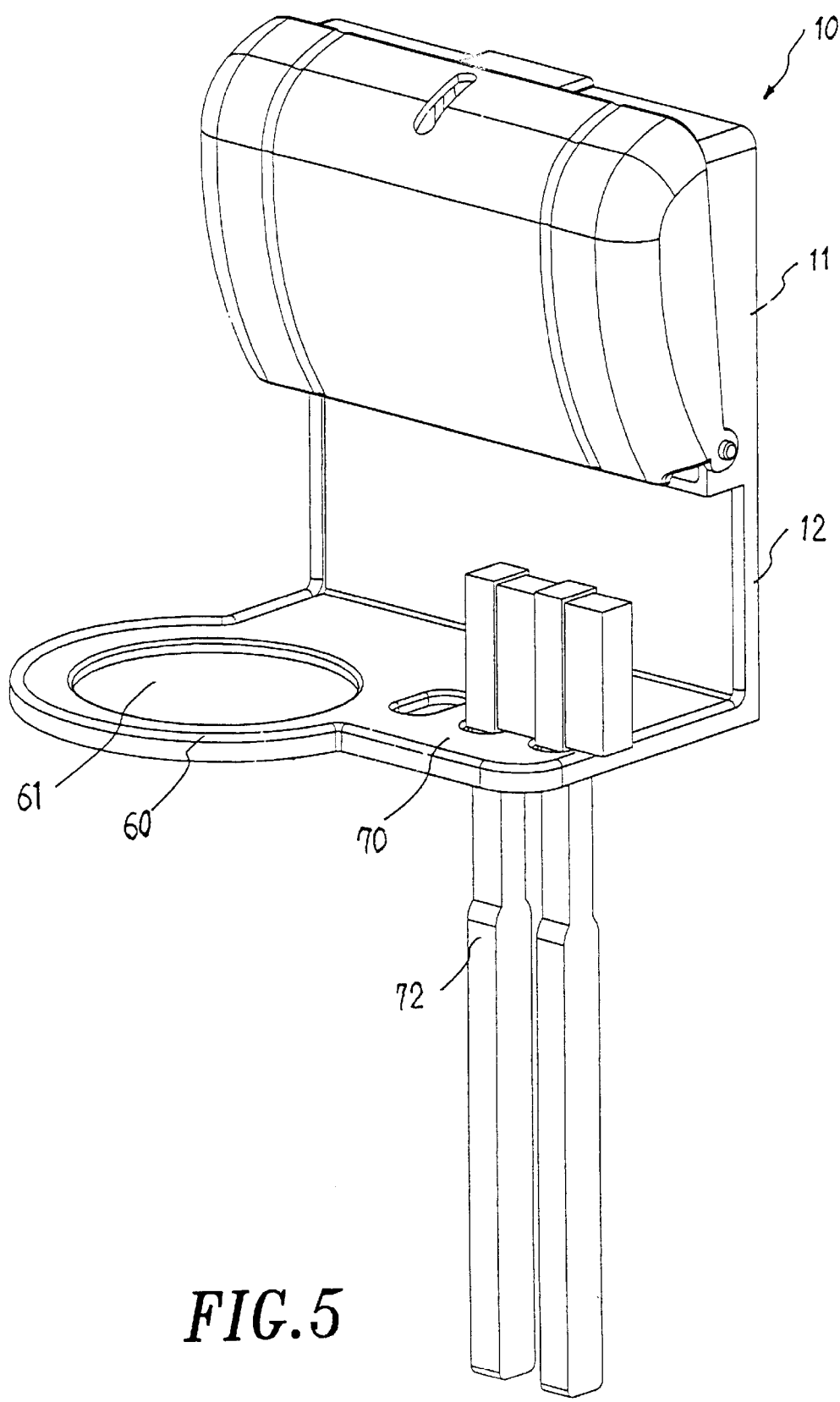
FIG. 5 is a schematic view of the fourth embodiments according to the invention.

In another embodiment shown in FIG. 5, the lower part 12 of the air freshener vessel 10 comprises a tooth mug holder 60 and a tooth brush holder 70, where, in addition to a holding hole 61 for holding tooth mug 62, there are several holding holes 71 for holding tooth brushes 72 or other tools.

Figure 6:
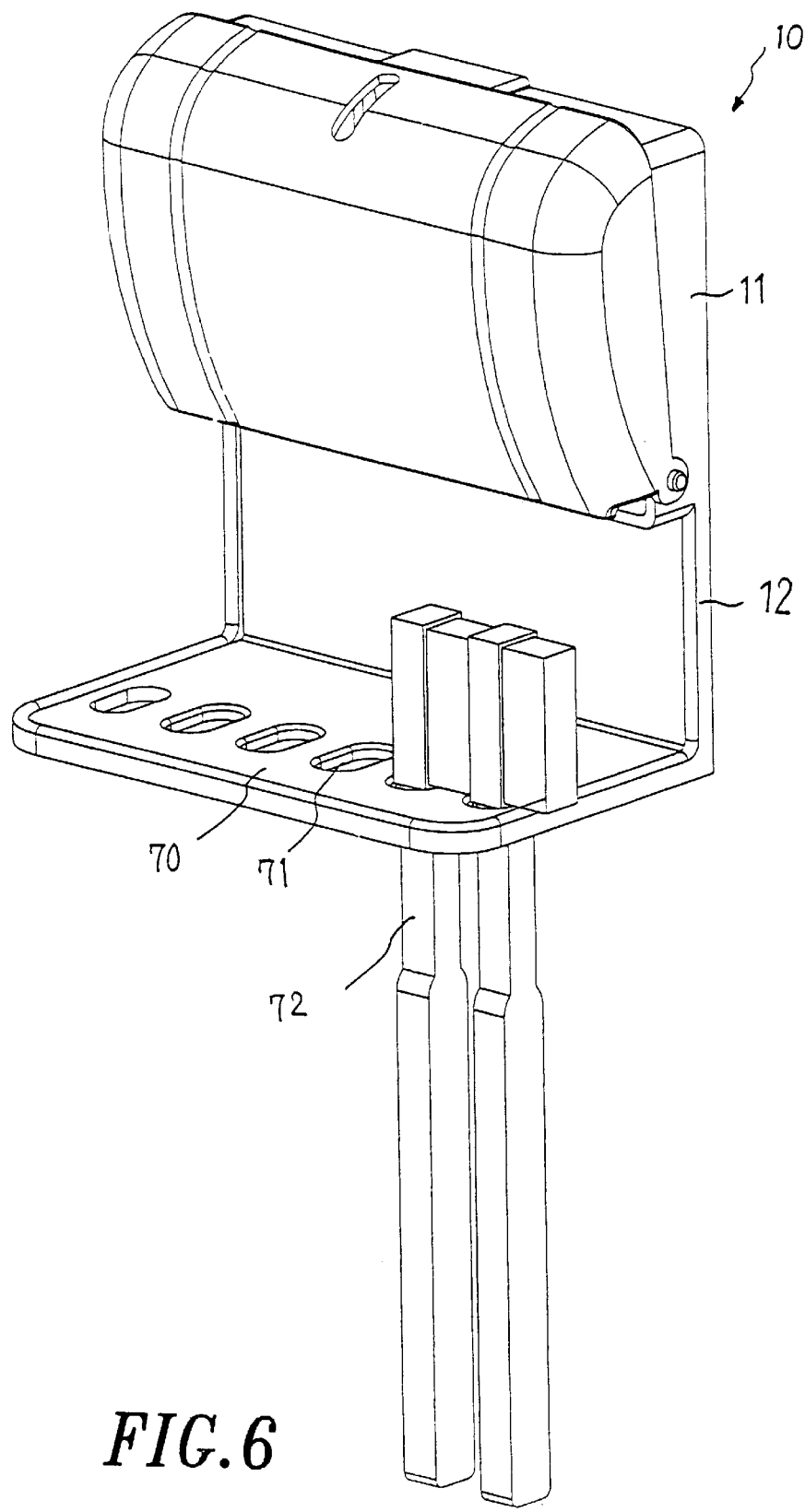
FIG. 6 is a schematic view of the fifth embodiments according to the invention.

In another embodiment shown in FIG. 6, the lower part 12 of the air freshener vessel 10 comprises a toothbrush holder 70 that has several holding holes 71 for holding toothbrushes or other tools.

Figure 7:
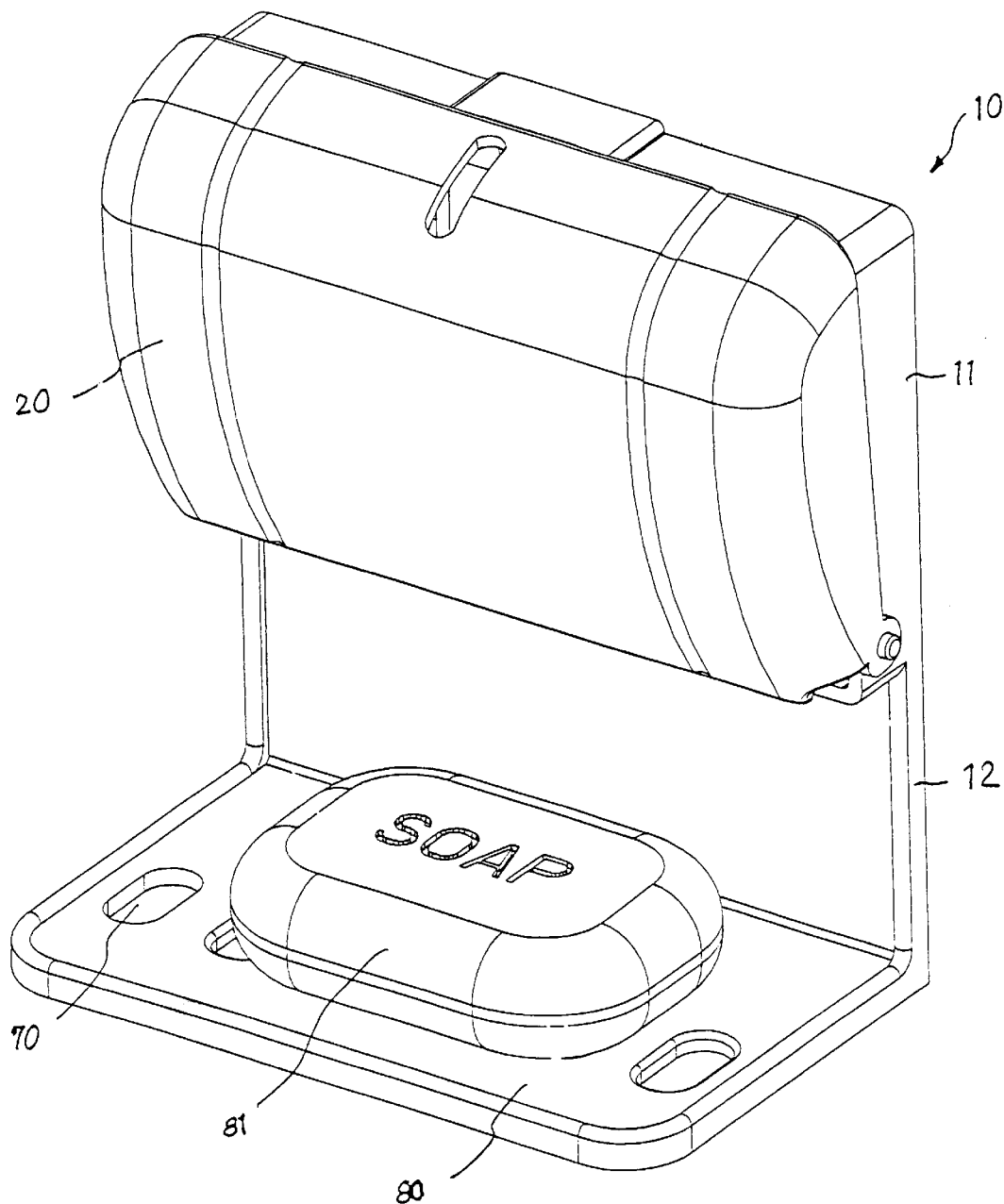
FIG. 7 is a schematic view of the sixth embodiments according to the invention.
Figure 8:
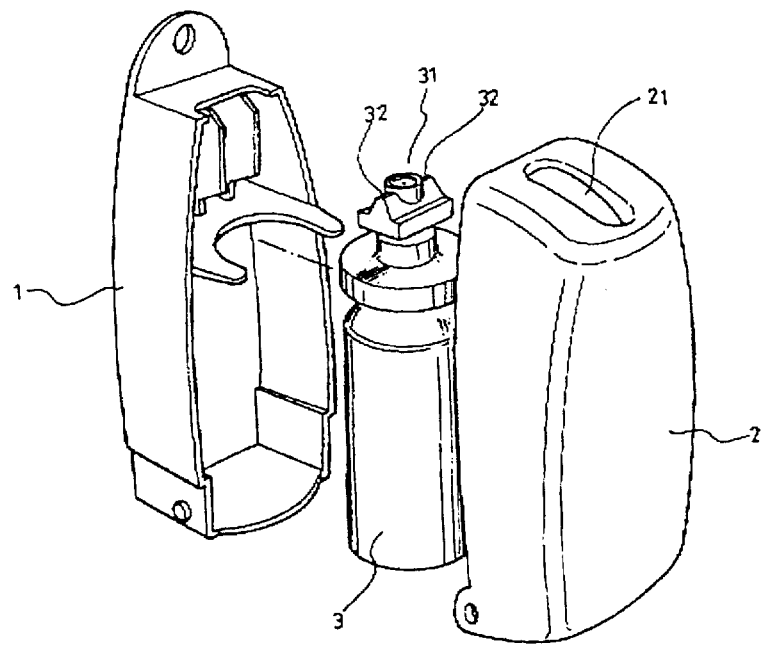
FIG. 8 is a schematic view of an embodiments described in ROP 88203043.
Figure 8:
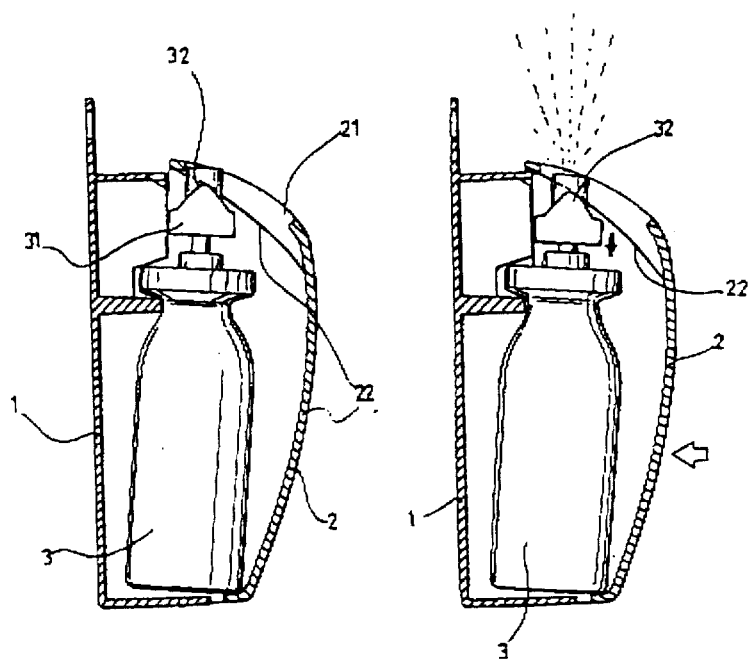

In the embodiment shown in FIG. 7, the lower part 12 of the air freshener vessel 10 comprises soap dish holder 80 that has a holding recess 81 for holding soap 81 and several holding holes 71 for holding tooth brushes or other tools.

The functional tools integrated in the lower part 12 of the air freshener vessel 10 can make various toilet products combine with one another into a unity so as to produce multi-functional effect, such that not only increases the added value of the commodity, but also can make the wall compact and good looking.

The above-described integration of the air freshener vessel 10 with the toilet paper roll holder 50, the tooth mug holder 60, the tooth brush holder 70 and/or the soap dish holder 80 can be formed by an integral mode such that the air freshener vessel 10 and the toilet paper roll holder 50, the air freshener vessel 10 and the tooth mug holder 60, the air freshener vessel 10 and the tooth brush holder 70 or the air freshener vessel 10 and the soap dish holder 80 can be made into a single product having combined function to adapt flexibly according to the demand.

Many changes and modifications in the above-described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A multi-functional assembly of toilet products, comprising:
   a main vessel body, consisting of a upper part and a lower part, wherein said upper part is provided with several compartments, and said lower part is extended from said upper part, and wherein, along the perpendicular direction on each of both lateral sides of said lower part, a side plate is provided, respectively; and arc guiding slots are provided at suitable place along the inner edge of each of said two side plates;
   a supporting shaft, both ends thereof being disposed in said arc guiding slots;

a pressing plate, provided with a slot on top end thereof; and a pressing block, provided at a suitable site on its top end with a nozzle corresponding with said slot;

wherein, as the pressing plate is pushed down, said pressing block can be pushed at the same time and it can in turn push the content such as a perfume, in said compartment to atomize an air freshener solution in said compartment out of said nozzle provided on said pressing block and release via said slot in said pressing plate, while the support shaft in said lower part can have toilet-paper roll disposed thereon.

2. A multi-functional assembly of toilet products recited in claim 1, wherein said lower part can be separated from said upper part and re-assembled.

3. A multi-functional assembly of toilet products recited in claim 1, comprises further on said two lateral plates a turn over cover, wherein pivotally engaging holes are provided on both side of said turn over cover, such that said pivotally engaging holes can correspond with through holes preset on said two lateral plates in a manner that said pivotally engaging holes can be engaged with said through holes via a button.

* * * * *